United States Patent
Kiuchi

(10) Patent No.: US 10,736,979 B2
(45) Date of Patent: Aug. 11, 2020

(54) STERILIZATION DEVICE

(71) Applicant: Nikkiso Co., Ltd., Tokyo (JP)

(72) Inventor: Hiroki Kiuchi, Hakusan (JP)

(73) Assignee: NIKKISO CO., LTD., Tokyo (JP)

(*) Notice: Subject to any disclaimer, the term of this patent is extended or adjusted under 35 U.S.C. 154(b) by 0 days.

(21) Appl. No.: 15/872,818

(22) Filed: Jan. 16, 2018

(65) Prior Publication Data

US 2018/0140728 A1    May 24, 2018

Related U.S. Application Data

(63) Continuation of application No. PCT/JP2016/075192, filed on Aug. 29, 2016.

(30) Foreign Application Priority Data

Sep. 7, 2015  (JP) .................. 2015-176158

(51) Int. Cl.
    *A61L 2/10*    (2006.01)
    *C02F 1/32*    (2006.01)
    *C02F 1/02*    (2006.01)

(52) U.S. Cl.
    CPC .................... *A61L 2/10* (2013.01);
         *C02F 1/02* (2013.01); *C02F 1/32* (2013.01);
         *C02F 1/325* (2013.01);
    (Continued)

(58) Field of Classification Search
    CPC ........ A61L 2/10; A61L 9/20; A61L 2202/122;
         C02F 1/02; C02F 1/325; C02F 1/32;
         C02F 2201/3227; C02F 2201/3222; C02F
         2203/04; C02F 2201/326; C02F 2303/10;
         Y02W 10/30
    See application file for complete search history.

(56) References Cited

U.S. PATENT DOCUMENTS 9,295,742 B2 * 3/2016 Rasooly .................. A61L 2/10
10,040,699 B2 * 8/2018 Smetona .................. C02F 1/008
2015/0336810 A1 11/2015 Smetona et al.

FOREIGN PATENT DOCUMENTS

CN     204111365 U     1/2015
JP     2001225067 A *  8/2001
                (Continued)

OTHER PUBLICATIONS

JP-2001225067-A Translation (Year: 2001).*
(Continued)

*Primary Examiner* — Sean E Conley
*Assistant Examiner* — Brendan A Hensel
(74) *Attorney, Agent, or Firm* — Muncy, Geissler, Olds & Lowe, P.C.

(57) ABSTRACT

A sterilization device includes: a treatment chamber with a discharge valve provided on a downstream side of the treatment chamber; a light source that irradiates a fluid stored temporarily in the treatment chamber with ultraviolet light; and a heat exchange chamber connected to an upstream side of the treatment chamber via a gate valve. The heat exchange chamber is thermally connected to the light source. The sterilization device may further include a heat pipe that thermally connects the light source and the heat exchange chamber. The heat pipe may be provided to extend vertically upward from the light source toward the heat exchange chamber.

6 Claims, 3 Drawing Sheets

(52) U.S. Cl.
CPC ... *A61L 2202/122* (2013.01); *C02F 2201/326* (2013.01); *C02F 2201/3222* (2013.01); *C02F 2201/3227* (2013.01); *C02F 2303/04* (2013.01); *C02F 2303/10* (2013.01); *Y02W 10/30* (2015.05)

(56) References Cited

FOREIGN PATENT DOCUMENTS

| | | | | |
|---|---|---|---|---|
| JP | 2001225067 | A | 8/2001 | |
| JP | 2014061483 | A | 4/2014 | |
| JP | 2014184430 | A | 10/2014 | |
| JP | 2014205082 | A * | 10/2014 | ............ C02F 1/325 |
| JP | 2014205082 | A | 10/2014 | |

OTHER PUBLICATIONS

JP-2014205082-A Translation (Year: 2014).*
Makeitfrom, Aluminum (Year: 2014).*
Makeitfrom, PMP (Year: 2015).*
MakeItFrom Copper data (Year: 0).*
Taiwanese Office Action with English Language Translation based on corresponding Application No. 105128628; dated Nov. 19, 2019.
Office Action dated Aug. 22, 2019 in CN Application No. 201680047698.X.
Office Action dated Apr. 9, 2020 in corresponding CN Application No. 201680047698.X.

* cited by examiner

STERILIZATION DEVICE

CROSS-REFERENCE TO RELATED APPLICATIONS

This application is a Continuation of co-pending Application No. PCT/JP2016/075192 filed on Aug. 29, 2016, for which priority is claimed under 35 U.S.C. § 120; and this application claims priority of Application No. 2015-176158, filed in Japan on Sep. 7, 2015 under 35 U.S.C. § 119; the entire content of all of which are incorporated herein by reference.

BACKGROUND OF THE INVENTION

1. Field of the Invention

The present invention relates to a sterilization device, and particularly to a device for irradiating a fluid with ultraviolet light for sterilization.

2. Description of the Related Art

Ultraviolet light is known for its sterilization capability, and devices for emitting ultraviolet light are used for sterilization treatment in the field of medical treatment, food processing, or the like. There are also devices used to irradiate a fluid, such as water, stored in a treatment tank with ultraviolet light so as to sterilize the fluid. Since a light source for emitting ultraviolet light is affected by heat generated during the light emission, the light source is used while being appropriately cooled. For example, the light source can be cooled by circulating the water stored in the treatment tank using a pump.

Although a water-cooling system, having higher cooling efficiency, would be desirable in order to appropriately cool a light source, if a drive source, such as a pump, or a passage needs to be newly provided for water cooling, it may cause an increase in the number of necessary parts or in power consumption due to driving of the pump. Also, in the field of medical treatment or food processing, various devices have been often installed already, so that a smaller device would be desirable in consideration of restriction of space or the like.

The present invention has been made in view of such a problem, and an illustrative purpose thereof is to provide a small sterilization device with a simplified means for cooling a light source.

SUMMARY OF THE INVENTION

A sterilization device according to an embodiment of the present invention includes: a treatment chamber with a discharge valve provided on a downstream side of the treatment chamber; a light source that irradiates a fluid stored temporarily in the treatment chamber with ultraviolet light; and a heat exchange chamber connected to an upstream side of the treatment chamber via a gate valve. The heat exchange chamber is thermally connected to the light source.

According to this embodiment, when a fluid stored in the treatment chamber is irradiated with ultraviolet light for sterilization treatment, by storing a fluid in the heat exchange chamber located on the upstream side of the treatment chamber, heat generated by the light source can be cooled using the fluid in the heat exchange chamber. Since the fluid stored in the heat exchange chamber is transferred to the treatment chamber so as to be sterilized next, and since a fluid is newly supplied to the heat exchange chamber, the light source can be cooled using a new fluid in each sterilization treatment. Therefore, according to the present embodiment, the light source can be suitably cooled using a relatively simple cooling means, without a circulation passage for water cooling.

The sterilization device may further include a heat pipe that thermally connects the light source and the heat exchange chamber.

The heat exchange chamber may be provided on a vertically upper side of the treatment chamber, and the heat pipe may be provided to extend vertically upward from the light source toward the heat exchange chamber.

The treatment chamber may be formed of a material transmitting ultraviolet light emitted by the light source.

The heat exchange chamber may be formed of a material having higher thermal conductivity than the material of the treatment chamber.

The sterilization device may further include a control device that controls operations of the light source, the discharge valve, and the gate valve. The control device may turn on the light source in a state where each of the treatment chamber and the heat exchange chamber stores a fluid, and both the discharge valve and the gate valve are closed.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

Figure 1:
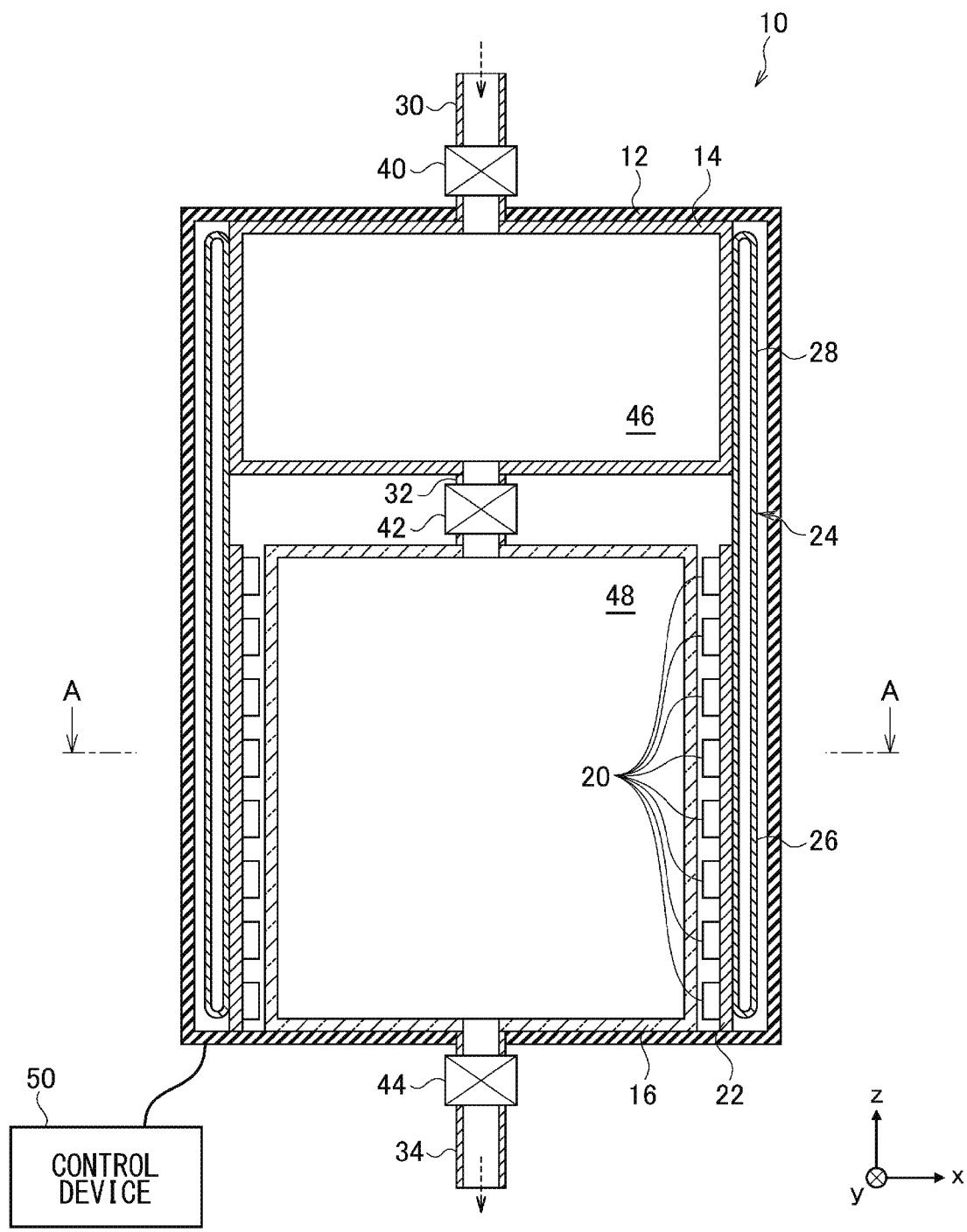
FIG. 1 is a vertical sectional view that schematically shows a configuration of a sterilization device according to an embodiment.

The invention will now be described by reference to the preferred embodiments. This does not intend to limit the scope of the present invention, but to exemplify the invention.

Hereinafter, a mode for carrying out the present invention will be described in detail with reference to the drawings. In the description, like reference characters designate like elements, and the same description thereof will be appropriately omitted.

Figure 2:
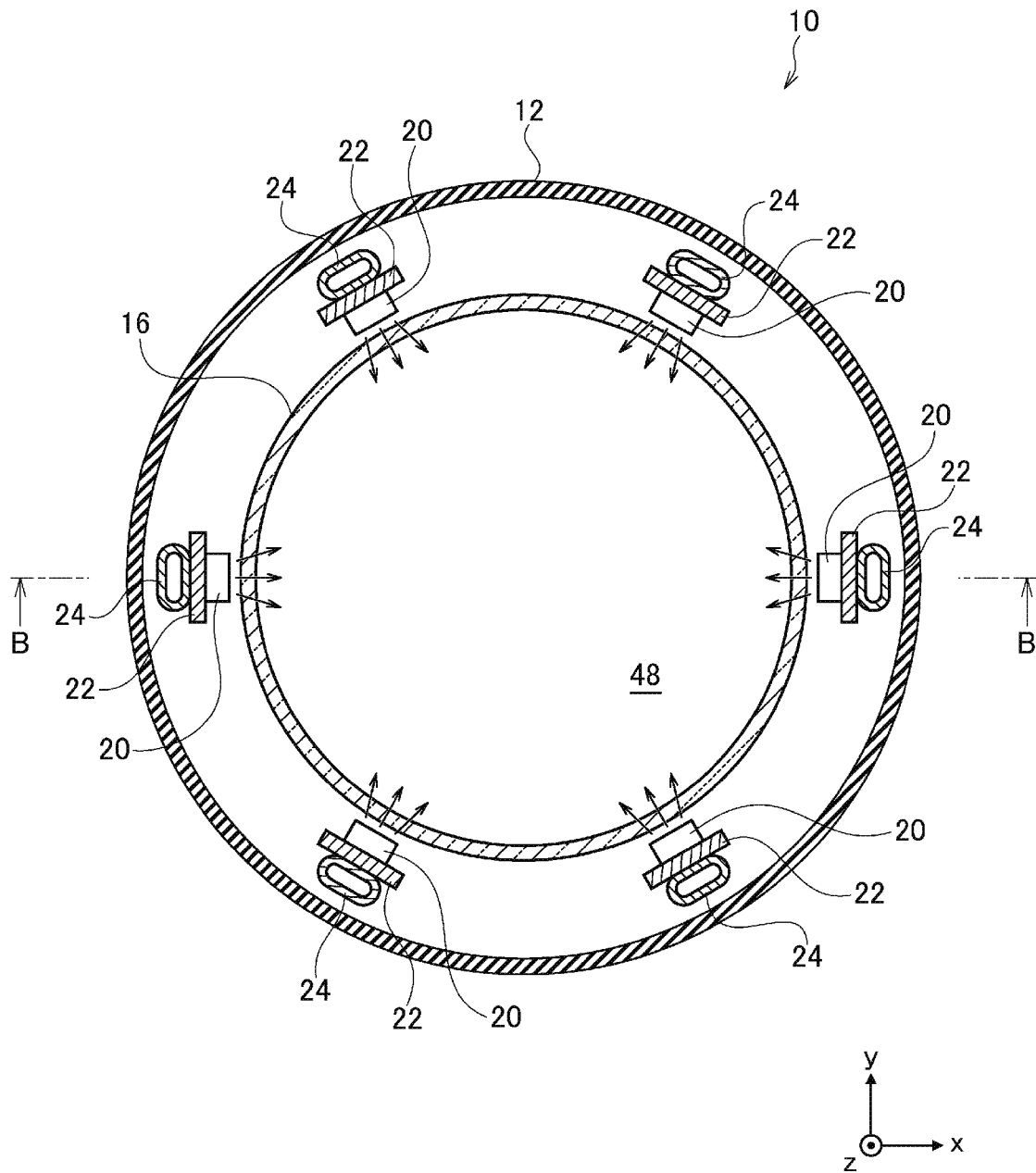
FIG. 2 is a horizontal sectional view that schematically shows a configuration of the sterilization device shown in FIG. 1.

FIG. 1 is a vertical sectional view that schematically shows a configuration of a sterilization device 10 according to an embodiment, and FIG. 2 is a horizontal sectional view that schematically shows a configuration of the sterilization device 10 shown in FIG. 1. FIG. 2 shows a section taken along line A-A in FIG. 1, and FIG. 1 shows a section taken along line B-B in FIG. 2. The sterilization device 10 is a device that stores a fluid, such as drinking water, in a treatment chamber 48 and irradiates the fluid with ultraviolet light for sterilization treatment. Light emitting elements 20 as a light source for emitting ultraviolet light are thermally connected to a heat exchange vessel 14 via substrates 22 and heat pipes 24. Accordingly, the sterilization device 10 can perform sterilization treatment while cooling the light emitting elements 20 with a fluid stored in a heat exchange chamber 46.

The sterilization device 10 comprises a casing 12, the heat exchange vessel 14, a treatment vessel 16, the light emitting elements 20, the substrates 22, the heat pipes 24, an inflow pipe 30, a connection pipe 32, a discharge pipe 34, an inflow valve 40, a gate valve 42, a discharge valve 44, and a control device 50.

The casing 12 has a cylindrical shape and houses the heat exchange vessel 14 and the treatment vessel 16 therein. The casing 12 is made of a metal material or resin material, for example. The inflow pipe 30 is provided on an upper end of the casing 12, and the discharge pipe 34 is provided on a lower end of the casing 12.

In the present specification, the side on which the inflow pipe 30 is provided will be referred to as the upstream side, and the side on which the discharge pipe 34 is provided will be referred to as the downstream side. Within the casing 12, the heat exchange vessel 14 is provided on the upstream side of the treatment vessel 16, and the treatment vessel 16 is provided on the downstream side of the heat exchange vessel 14. Also, in the present embodiment, the inflow pipe 30 is provided on a vertically upper side, and the discharge pipe 34 is provided on a vertically lower side. Namely, in the present embodiment, the upstream side means the vertically upper side, and the downstream side means the vertically lower side.

The heat exchange vessel 14 has a cylindrical shape corresponding to the casing 12 and forms the heat exchange chamber 46. The heat exchange vessel 14 would be suitably constituted by a member having high thermal conductivity and is formed of a metal material, such as copper (Cu) and aluminum (Al). To the upstream side of the heat exchange vessel 14 is connected the inflow pipe 30, and to the downstream side of the heat exchange vessel 14 is connected the connection pipe 32. Also, to the heat exchange vessel 14, a heat radiation part 28 of each heat pipe 24 is thermally connected.

The treatment vessel 16 has a cylindrical shape corresponding to the casing 12 and forms the treatment chamber 48. The treatment vessel 16 would be suitably constituted by a member having high ultraviolet light transmittance and is formed of amorphous fluororesin or a glass material, such as quartz ($SiO_2$). To the upstream side of the treatment vessel 16 is connected the connection pipe 32, and to the downstream side of the treatment vessel 16 is connected the discharge pipe 34. Also, outside the treatment vessel 16, the light emitting elements 20 are provided so as to surround the treatment vessel 16.

Each light emitting element 20 is an light emitting diode (LED) that emits ultraviolet light of which the center wavelength or peak wavelength falls within a range of about 200 nm to 350 nm. The light emitting elements 20 may suitably be LEDs that emit ultraviolet light of which the wavelength falls within a range of about 260 nm to 270 nm, which has high sterilization efficiency. As such an ultraviolet LED, one using aluminum gallium nitride (AlGaN) is known, for example.

A plurality of the light emitting elements 20 are mounted on a substrate 22 provided outside the treatment vessel 16 and are disposed to face the direction of ultraviolet light emission toward a fluid within the treatment chamber 48. As shown in FIG. 1, each substrate 22 extends in a vertical direction (z-direction) along an outer wall of the treatment vessel 16, and a plurality of the light emitting elements 20 are mounted on the substrate 22 so as to be aligned in a z-direction. Also, the substrates 22, on each of which a plurality of the light emitting elements 20 are mounted, are disposed around the treatment vessel 16 at different positions in a circumferential direction, as shown in FIG. 2. For example, the substrates 22 may be disposed at six positions that each are shifted from another by 60 degrees in a circumferential direction. Accordingly, the light emitting elements 20 are set to emit ultraviolet light equally over the entire treatment chamber 48.

Each substrate 22 would be suitably constituted by a member having high thermal conductivity, and copper or aluminum may be used as a base material thereof, for example. To each substrate 22, an endothermic part 26 of a heat pipe 24 is connected. Accordingly, heat generated during the light emission of the light emitting elements 20 is transmitted to the heat pipes 24 via the substrates 22.

Each heat pipe 24 is a metal pipe having a hollow structure, and a volatile heat medium is sealed therein. Each heat pipe 24 includes the endothermic part 26 and the heat radiation part 28, and it absorbs heat when the heat medium therein evaporates near the endothermic part 26 and radiates heat when the heat medium therein condenses near the heat radiation part 28. Each heat pipe 24 is disposed so that the endothermic part 26 is located on the vertically lower side and the heat radiation part 28 is located on the vertically upper side, and the endothermic part 26 is thermally connected to a substrate 22, and the heat radiation part 28 is thermally connected to the outer wall of the heat exchange vessel 14.

In the inflow pipe 30, the inflow valve 40 is provided. When the inflow valve 40 is opened, a fluid to be sterilized flows into the heat exchange chamber 46. In the connection pipe 32, the gate valve 42 is provided. When the gate valve 42 is opened, the fluid to be sterilized is transferred from the heat exchange chamber 46 to the treatment chamber 48. Also, in the discharge pipe 34, the discharge valve 44 is provided. When the discharge valve 44 is closed, the fluid to be sterilized is stored in the treatment chamber 48. After the sterilization treatment is performed in the treatment chamber 48, by opening the discharge valve 44, the sterilized fluid flows out through the discharge pipe 34.

The control device 50 controls the operations of the light emitting elements 20, inflow valve 40, gate valve 42, and discharge valve 44. The control device 50 opens the inflow valve 40 and the gate valve 42 to allow a fluid to be sterilized to flow into the heat exchange chamber 46 and the treatment chamber 48. The control device 50 closes the gate valve 42 and the discharge valve 44 to store a fluid to be sterilized in the treatment chamber 48 and also store a fluid used for water cooling in the heat exchange chamber 46. Also, the control device 50 opens the discharge valve 44 while keeping the gate valve 42 closed so as to allow only a fluid sterilized in the treatment chamber 48 to flow outside.

Figure 3:
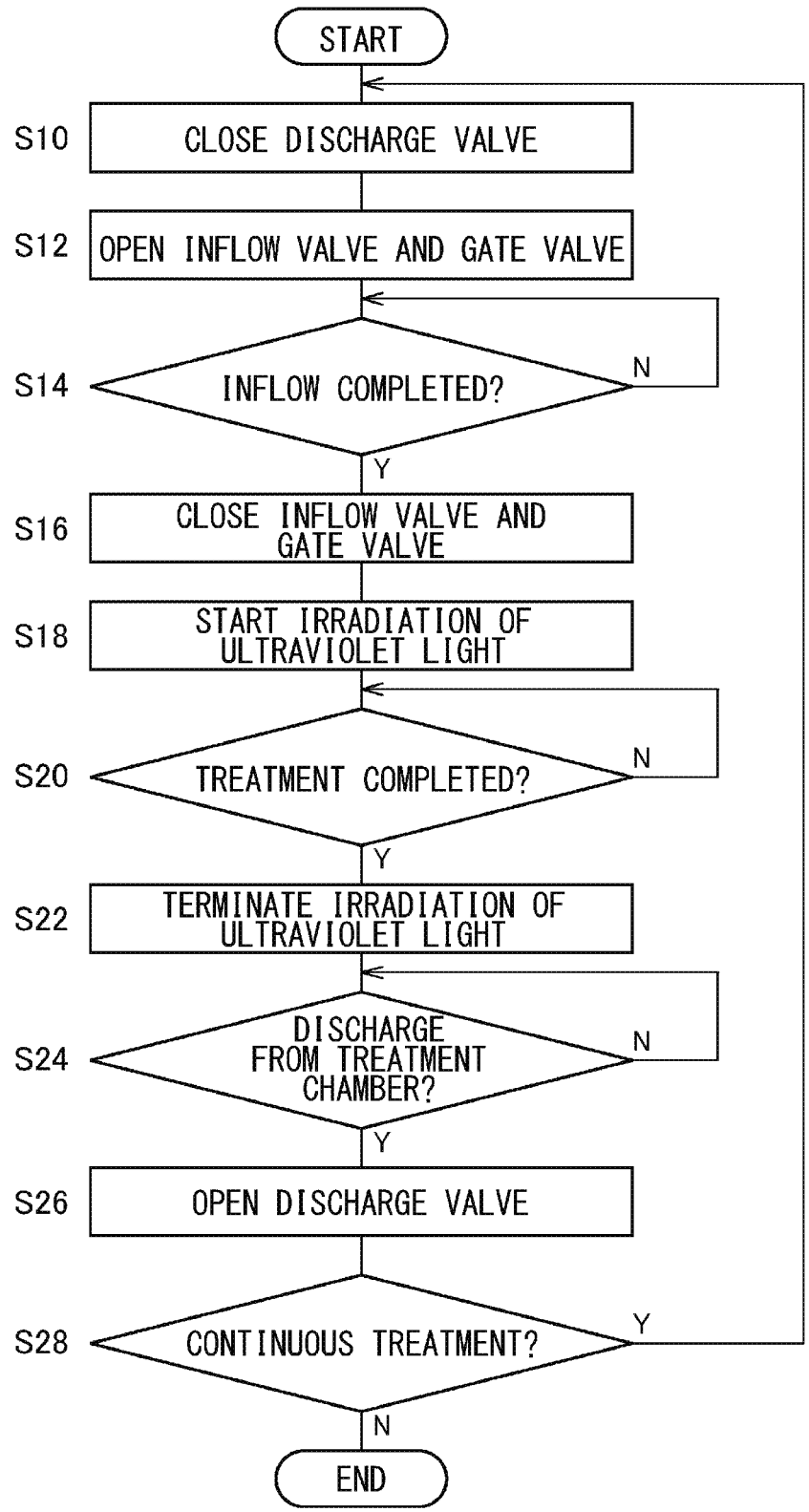
FIG. 3 is a flowchart that shows an operational process of the sterilization device.

FIG. 3 is a flowchart that shows an operational process of the sterilization device 10. First, the discharge valve 44 is closed (S10) and the inflow valve 40 and the gate valve 42 are opened (S12) so as to allow a fluid to be sterilized to flow into the heat exchange chamber 46 and the treatment chamber 48. The completion of the inflow of the fluid to the heat exchange chamber 46 and the treatment chamber 48 is waited (N at S14) and, when the inflow is completed (Y at S14), the inflow valve 40 and the gate valve 42 are closed (S16), and the light emitting elements 20 are turned on to start irradiation of ultraviolet light (S18). The irradiation of ultraviolet light is continued until the sterilization treatment is completed (N at S22), and, when a period of time required for completion of the sterilization treatment has elapsed (Y at S22), the light emitting elements 20 are turned off to terminate the irradiation of ultraviolet light (S22). Thereafter, timing for discharging the sterilized fluid from the treatment chamber 48 is waited (N at S24), and, at the timing therefor (Y at S24), the discharge valve 44 is opened to discharge the sterilized fluid (S26). If continuous treatment is necessary (Y at S28), the process of S10 through S26 will be repeated, and, if continuous treatment is unnecessary (N at S28), the process of this flowchart will be terminated.

According to the present embodiment, since the light emitting elements 20 are thermally connected to the heat exchange chamber 46 via the heat pipes 24, the light emitting elements 20 can be subjected to water cooling using the fluid stored in the heat exchange chamber 46. Since the fluid stored in the heat exchange chamber 46 is exchanged when the fluid is made to flow into the treatment chamber 48, a circulation passage for water cooling or a pump for circulating cooling water need not be newly provided. Therefore, according to the present embodiment, a sufficient cooling effect can be obtained using a water-cooling system, of which a means for cooling the light source can be simplified.

According to the present embodiment, since the treatment chamber 48 used for ultraviolet light irradiation and the heat exchange chamber 46 used for cooling are separately provided, a sufficient cooling effect can be obtained with a simple structure. Since the wall surfaces of the treatment chamber 48 are formed of fluororesin, silica glass, or the like for transmitting ultraviolet light and have low thermal conductivity, heat radiation through the wall surfaces of the treatment chamber 48 is difficult. The treatment chamber 48 could be used as a heat exchange chamber by providing a heat sink within the treatment chamber 48 or by disposing the light source within the treatment chamber 48; however, if such a configuration is employed, a complicated structure will be required to make the treatment chamber 48 watertight. Meanwhile, according to the present embodiment, since the light source is disposed outside the treatment chamber 48, a watertight structure can be easily obtained only by preparing a vessel made of a material for transmitting ultraviolet light, and a water-cooling effect can be obtained using the heat exchange chamber 46 with a simple structure.

According to the present embodiment, since the gate valve 42 is provided between the heat exchange chamber 46 and the treatment chamber 48, only a fluid sterilized in the treatment chamber 48 can be discharged. If the gate valve 42 is not provided, a fluid stored in the heat exchange chamber 46, which has not been irradiated with ultraviolet light, may be discharged together with the sterilized fluid. In the present embodiment, however, since the heat exchange chamber 46 and the treatment chamber 48 are separated by the gate valve 42, only a fluid that has been sufficiently sterilized in the treatment chamber 48 can be discharged, so that the sterilization effect on the discharged fluid can be improved.

According to the present embodiment, by employing copper, having high thermal conductivity, as the material of the wall surfaces of the heat exchange chamber 46, a sterilization effect of copper ions can be obtained. Therefore, according to the present embodiment, the sterilization effect of copper ions and the sterilization effect of ultraviolet light irradiation can be combined, so that the sterilization capability can be improved.

The present invention has been described with reference to the embodiment. It should be understood by those skilled in the art that the invention is not limited to the above-described embodiment and that various modifications could be developed on the basis of various design modifications and such modifications also fall within the scope of the present invention.

In a modification, the inflow valve 40 need not necessarily be provided.

In a modification, an additional cooling device may be provided for the heat exchange vessel 14. For example, a Peltier device or a fan for air cooling may be added to the heat exchange vessel 14.

In a modification, the sterilization device may be used for purification treatment for decomposing an organic substance included in a fluid by irradiation of ultraviolet light.

It should be understood that the invention is not limited to the above-described embodiment, but may be modified into various forms on the basis of the spirit of the invention. Additionally, the modifications are included in the scope of the invention.

What is claimed is:

1. A sterilization device, comprising:
   a treatment chamber with a discharge valve provided on a downstream side of the treatment chamber;
   a light source that irradiates a fluid stored temporarily in the treatment chamber with ultraviolet light, wherein the light source comprises a plurality of light emitting elements surrounding the treatment chamber along a vertical wall of the treatment chamber; and
   a heat exchange chamber connected to an upstream side of the treatment chamber via a gate valve, wherein the heat exchange chamber is disposed entirely on a top of the treatment chamber without overlapping with the treatment chamber in a lateral direction,
   wherein the heat exchange chamber is thermally connected to the light source.

2. The sterilization device of claim 1, further comprising a heat pipe that thermally connects the light source and the heat exchange chamber.

3. The sterilization device of claim 2, wherein the heat pipe is provided to extend vertically upward from the light source toward the heat exchange chamber.

4. The sterilization device of claim 1, wherein the treatment chamber is formed of a material transmitting ultraviolet light emitted by the light source.

5. The sterilization device of claim 4, wherein the heat exchange chamber is formed of a material having higher thermal conductivity than the material of the treatment chamber.

6. The sterilization device of claim 1, further comprising a control device that controls operations of the light source, the discharge valve, and the gate valve, wherein the control device turns on the light source in a state where each of the treatment chamber and the heat exchange chamber stores a fluid, and both the discharge valve and the gate valve are closed.

* * * * *